(12) United States Patent
Hashimoto (10) Patent No.: US 9,161,741 B2
(45) Date of Patent: Oct. 20, 2015

(54) ULTRASONIC IMAGE PROCESSING APPARATUS, ULTRASONIC DIAGNOSTIC APPARATUS, AND ULTRASONIC IMAGE PROCESSING METHOD

(75) Inventor: Shinichi Hashimoto, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 79 days.

(21) Appl. No.: 13/107,323

(22) Filed: May 13, 2011

(65) Prior Publication Data
US 2011/0282207 A1    Nov. 17, 2011

(30) Foreign Application Priority Data

May 17, 2010    (JP) .................................. 2010-113523

(51) Int. Cl.
*A61B 8/00*    (2006.01)
*A61B 8/08*    (2006.01)

(52) U.S. Cl.
CPC ............... *A61B 8/466* (2013.01); *A61B 8/0883* (2013.01); *A61B 8/463* (2013.01); *A61B 8/483* (2013.01); *A61B 8/469* (2013.01); *A61B 8/523* (2013.01)

(58) Field of Classification Search
CPC ...... A61B 8/0883; A61B 8/463; A61B 8/466; A61B 8/469; A61B 8/483; A61B 8/523
USPC .......... 600/407–475; 382/128, 130–134, 173, 382/174, 254–308, 318–321; 345/1.1–9, 345/156–184, 204–210, 418–472.3, 345/501–522, 690–699
See application file for complete search history.

(56) References Cited

U.S. PATENT DOCUMENTS

| 2004/0249270 A1* | 12/2004 | Kondo et al. ................. 600/425 |
| 2007/0167796 A1* | 7/2007 | Yoshimura ..................... 600/455 |
| 2008/0154952 A1 | 6/2008 | Waldinger et al. |
| 2009/0198134 A1 | 8/2009 | Hashimoto et al. |

FOREIGN PATENT DOCUMENTS

| JP | 2004-283373 A | 10/2004 |
| JP | 2007-503857 A | 3/2007 |
| JP | 2008-173216 A | 7/2008 |

OTHER PUBLICATIONS

Office Action issued on Jan. 7, 2014 in a basic/ corresponding Japanese Patent Application No. 2010-113523 (with English Translation).

Combined Chinese Office Action and Search Report issued Feb. 28, 2014 in Patent Application No. 201110126841.3 with English Translation.

* cited by examiner

*Primary Examiner* — Mark Remaly
(74) *Attorney, Agent, or Firm* — Oblon, McClelland, Maier & Neustadt, L.L.P.

(57) ABSTRACT

According to one embodiment, an apparatus includes a slice image generation unit, a three-dimensional image generation unit, a display unit, a setting unit, an updating unit, and a changing unit. The slice image generation unit generates the data of slice images based on a volume data. The three-dimensional image generation unit generates the data of a three-dimensional image based on the volume data. The display unit displays the slice images and the three-dimensional image. The setting unit sets the vector on the first slice image of the displayed slice images in accordance with an instruction from an operator. The updating unit updates the displayed three-dimensional image based on the vector. The changing unit changes the position of a slice of a remaining slice image of the displayed slice images to a position where the slice intersects the vector and is perpendicular to the slice of the first slice image.

8 Claims, 8 Drawing Sheets

FIG. 1

Display layout

FIG. 2

Initial arrangement of A, B, and C planes

When C plane intersects midpoint P3 of setting vector Ve

FIG. 13

First, second, and third C planes respectively intersecting start point P1,
end point P2,
and midpoint P3
of setting vector Ve are simultaneously set

FIG. 14

ULTRASONIC IMAGE PROCESSING APPARATUS, ULTRASONIC DIAGNOSTIC APPARATUS, AND ULTRASONIC IMAGE PROCESSING METHOD

CROSS-REFERENCE TO RELATED APPLICATIONS

This application is based upon and claims the benefit of priority from Japanese Patent Application No. 2010-113523, filed May 17, 2010; the entire contents of which are incorporated herein by reference.

FIELD

Embodiments described herein relate generally to an ultrasonic image processing apparatus, ultrasonic diagnostic apparatus, and ultrasonic image processing method.

BACKGROUND

For image diagnosis using ultrasonic images, three-dimensional images are generated and displayed based on volume data generated by ultrasonic scanning. As a means for easily generating a desired three-dimensional image, a function of simultaneously setting a viewing direction and a target region (to be referred to as an extraction region hereinafter) for three-dimensional image processing on an MPR image has appeared on the market.

Typically, the above simultaneous setting function displays, in parallel, one three-dimensional image and three MPR images perpendicular to each other. MPR images are displayed to set a viewing direction and an extraction region. The slice positions of MPR images are fixed unless changed by the operator. A three-dimensional image is a two-dimensional display image generated based on a set viewing direction and extraction region.

The following is a procedure for setting operation by the operator for a viewing direction and an extraction region using the above simultaneous setting function. First of all, the operator selects an image, from the three displayed MPR images, which allows easy designation of an extraction region. The operator then moves the mouse cursor onto the selected MPR image, and clicks a mouse button at a position corresponding to one end of an extraction region to designate the start point of a vector (a vector for setting a viewing direction and an extraction region; to be written as a setting vector hereinafter). The operator then moves the mouse cursor to a position corresponding to the other end of the extraction region to designate the end point of the setting vector. The vector connecting the designated start point to the designated end point is set as a setting vector. When the setting vector is set on one MPR image, the projections of the setting vector are displayed on the remaining MPR images. The operator adjusts the three-dimensional direction and length of the setting vector by adjusting the directions and lengths of the setting vectors projected on the remaining MPR images with the mouse cursor.

However, since a setting vector is set on a displayed MPR image, the three-dimensional direction of the setting vector is limited within a slice of the displayed MPR image. For this reason, when the operator wants to direct the setting vector to the outside of the slice of the display MPR image, he/she needs to adjust the slice of the MPR image and re-adjust the direction of the setting vector on the MPR image after adjustment. As described above, in order to optimally set a setting vector in a three-dimensional manner, it is necessary to repeat adjustment of a slice of an MPR image and adjustment of a vector on the MPR image.

DETAILED DESCRIPTION

In general, according to one embodiment, an ultrasonic image processing apparatus includes a storage unit, a slice image generation unit, a three-dimensional image generation unit, a display unit, a setting unit, an updating unit, and a changing unit. The storage unit stores volume data generated by ultrasonic scanning. The slice image generation unit generates the data of a plurality of slice images corresponding to a plurality of predetermined slices based on the volume data. The three-dimensional image generation unit generates the data of a three-dimensional image associated with a predetermined viewing direction based on the volume data. The display unit displays the slice images and the three-dimensional image. The setting unit sets the vector on the first slice image of the displayed slice images in accordance with an instruction from an operator. The updating unit updates the displayed three-dimensional image based on the set vector. The changing unit changes the position of a slice of a remaining slice image of the displayed slice images to a position where the slice intersects the set vector and is perpendicular to the slice of the first slice image.

An ultrasonic image processing apparatus, ultrasonic diagnostic apparatus, and ultrasonic image processing method according to this embodiment will be described below with reference to the views of the accompanying drawing.

Figure 1:
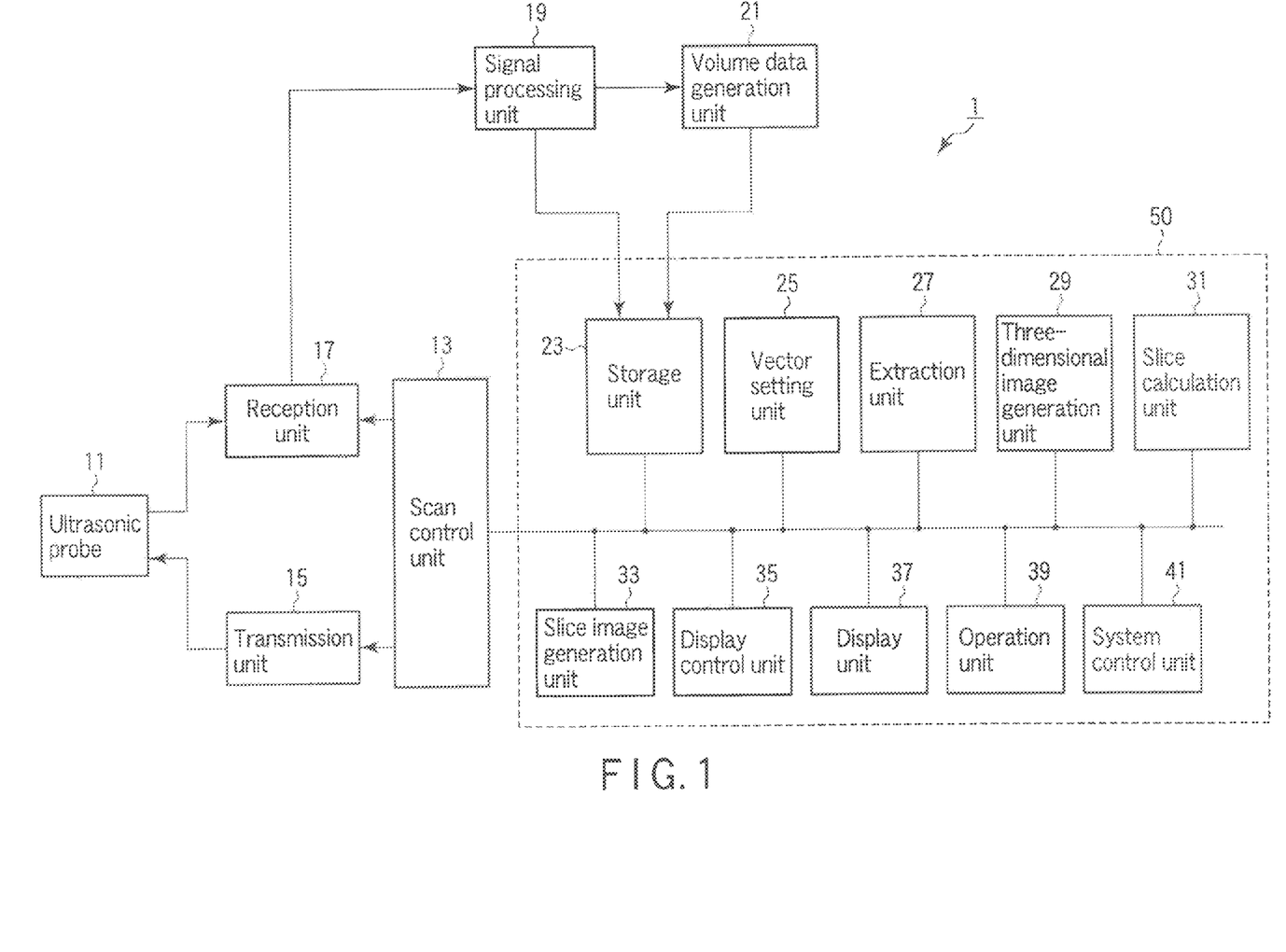
FIG. 1 is a block diagram showing the arrangement of an ultrasonic image processing apparatus and ultrasonic diagnostic apparatus according to this embodiment.

FIG. 1 is a block diagram showing the arrangement of an ultrasonic diagnostic apparatus 1 and ultrasonic image processing apparatus 50 according to this embodiment. As shown in FIG. 1, the ultrasonic diagnostic apparatus 1 includes an ultrasonic probe 11, a scan control unit 13, a transmission unit 15, a reception unit 17, a signal processing unit 19, a volume data generation unit 21, a storage unit 23, a vector setting unit 25, an extraction unit 27, a three-dimensional image generation unit 29, a slice calculation unit 31, a slice image generation unit 33, a display control unit 35, a display unit 37, an operation unit 39, and a system control unit 41.

The ultrasonic probe 11 is of an electronic scan type. The ultrasonic probe 11 receives driving pulses from the transmission unit 15 to generate ultrasonic waves. The ultrasonic waves are sequentially reflected by the discontinuity points (echo source) of acoustic impedance of an internal body tissue of a subject. The ultrasonic probe 11 receives the reflected ultrasonic waves. Upon receiving the ultrasonic waves, the ultrasonic probe 11 converts them into an echo signal (electrical signal) originating from the received ultrasonic waves, and outputs the echo signal.

The scan control unit 13 controls the transmission unit 15 and the reception unit 17 to scan the subject with ultrasonic waves via the ultrasonic probe 11. The scan control unit 13, the transmission unit 15, and the reception unit 17 constitute a scanning unit which scans the subject with ultrasonic waves via the ultrasonic probe 11.

The transmission unit 15 repeatedly transmits driving pulses to the ultrasonic probe 11 under the control of the scan control unit 13. More specifically, the transmission unit 15 repeatedly generates rate pulses for each channel. The transmission unit 15 gives each generated rate pulse a delay time necessary to form an ultrasonic transmission beam associated with a predetermined transmission direction and transmission focus. This delay time is determined, for example, for each transducer in accordance with a transmission direction and a transmission focus position. The transmission unit 15 then generates transmission driving pulses at the timing based on each delay rate pulse, and supplies the generated driving pulses to each transducer. Upon receiving driving pulses, each transducer generates ultrasonic waves. With this operation, the ultrasonic probe 11 emits an ultrasonic transmission beam associated with a predetermined transmission direction and transmission focus position.

The reception unit 17 repeatedly receives echo signals originating from ultrasonic waves reflected by the subject via the ultrasonic probe 11 under the control of the scan control unit 13. Upon receiving an echo signal, the reception unit 17 generates a reception signal associated with the ultrasonic beam. More specifically, the reception unit 17 receives an echo signal from the ultrasonic probe 11, amplifies the received echo signal, and converts the amplified echo signal from analog to digital. The reception unit 17 then stores the digitally converted echo signal in a digital memory. A digital memory is provided for each transducer. An echo signal is stored at an address, on the digital memory corresponding to the transducer from which the echo signal is received, which corresponds to the reception time of the echo signal. The reception unit 17 reads out and adds each echo signal from an address corresponding to a predetermined reception focus position. By repeating this addition processing while changing the reception focus position along an ultrasonic transmission beam, the reception unit 17 generates an echo signal (to be referred to as a reception signal hereinafter) corresponding to the ultrasonic reception beam along a predetermined reception direction. The generated reception signal is supplied to the signal processing unit 19.

The signal processing unit 19 performs B-mode processing for the reception signal. More specifically, the signal processing unit 19 performs logarithmic compression or envelope detection processing for the reception signal. The reception signal having undergone logarithmic amplification or envelope detection processing is called a B-mode signal. The B-mode signal is supplied to the volume data generation unit 21.

The volume data generation unit 21 generates volume data associated with the subject based on the B-mode signal. More specifically, the volume data generation unit 21 interpolates the data of a data loss portion by placing the B-mode signal on a scan conversion memory in accordance with the position information of the signal. Performing this placement processing and interpolation processing will generate volume data. Each pixel constituting the volume data has a luminance value corresponding to the intensity of the originating echo signal. The volume data is supplied to the storage unit 23.

The storage unit 23 stores the volume data associated with the subject. The storage unit 23 further stores a dedicated program for automatic slice changing processing (ultrasonic image processing) to be described later.

The vector setting unit 25 sets a setting vector in the volume data in accordance with an instruction issued by the operator via the operation unit 39. The setting vector is used to set the viewing direction of a three-dimensional image and an extraction region as a target region of the three-dimensional image. The vector setting unit 25 can also adjust the positions of the start and end points of the setting vector, i.e., the length and direction of the setting vector, in accordance with an instruction issued by the operator via the operation unit 39.

The extraction unit 27 sets an extraction region having a range corresponding to the setting vector in the volume data, and extracts the data of the set extraction region from the volume data. The three-dimensional image generation unit 29 generates the data of a three-dimensional image having the setting vector as a viewing direction based on the data of the extraction region. Note that the three-dimensional image generation unit 29 can also generate the data of a three-dimensional image associated with the preset viewing direction or extraction region from volume data. The three-dimensional image generation unit 29 can also generate the data of a three-dimensional image from the overall volume data.

The slice calculation unit 31 calculates an MPR slice in accordance with the setting vector. The slice image generation unit 33 generates the data of a slice image associated with the calculated slice based on the volume data. The slice image generation unit 33 generates the data of the slice image by performing MPR (Multi-Planar Reconstruction) processing for the volume data. The slice image generated by MPR processing will be referred to as an MPR image hereinafter. Note that the slice image generation unit 33 can also generate the data of an MPR image associated with a preset slice.

The display control unit 35 displays an MPR image and a three-dimensional image on the display unit 37 in a predetermined layout. The display control unit 35 updates the displayed three-dimensional image in accordance with the setting vector set by the operator via the operation unit 39. The display control unit 35 also changes the displayed slice of the MPR image into a slice calculated in accordance with the settings of the setting vector. The display unit 37 displays the MPR image and the three-dimensional image in the predetermined layout under the control of the display control unit 35. The display unit 37 is formed by a display device such as a CRT display, liquid crystal display, organic EL display, or plasma display.

The operation unit 39 inputs various kinds of instructions and information from the operator via an input device. The input device includes a keyboard, a mouse, and various kinds of switches. For example, the operation unit 39 is used for the designation of the start and end points of a setting vector, which is performed to set a setting vector.

The system control unit 41 functions as the main unit of the ultrasonic diagnostic apparatus 1. More specifically, the system control unit 41 reads out the dedicated program from the storage unit 23, and executes the read dedicated program. The execution of the dedicated program will make the system control unit 41 control each unit in accordance with the procedure indicated by the dedicated program so as to execute automatic slice changing processing.

Note that the storage unit 23, the vector setting unit 25, the extraction unit 27, the three-dimensional image generation unit 29, the slice calculation unit 31, the slice image generation unit 33, the display control unit 35, the display unit 37, the operation unit 39, and the system control unit 41 constitute the ultrasonic image processing apparatus 50.

An example of the operation of the ultrasonic diagnostic apparatus 1, ultrasonic image processing apparatus 50, and ultrasonic image processing executed under the control of the system control unit 41 will be described by taking a clinical application to the heart as an example. Assume also that the heart is to be observed by an apical approach. Note that the region to which this embodiment is applied is not limited to the heart, but can be applied to any region of the subject.

Figure 2:
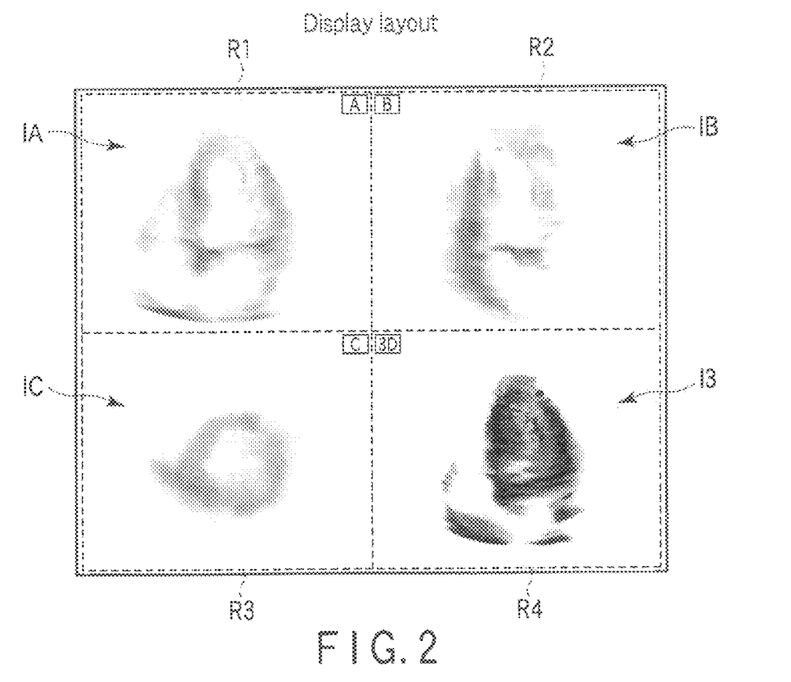
FIG. 2 is a view showing an example of the layout of 4-image display displayed on a display unit in FIG. 1.

Assume that in this embodiment, the heart is observed in a 4-image display layout. FIG. 2 is a view showing an example of a 4-image display layout. As shown in FIG. 2, four image display areas are assigned to the display window. Three MPR images IA, IB, and IC which are perpendicular to each other are respectively displayed in three image display areas R1, R2, and R3. The three MPR images IA, IB, and IC have three slices which are perpendicular to each other. In this case, the three slices will be referred to as A, B, and C planes, respectively, according to custom. The MPR image IA (to be referred to as the A plane image hereinafter), the MPR image IB (to be referred to as the B plane image hereinafter), and the MPR image IC (to be referred to as the C plane image hereinafter) are respectively displayed in the first, second, and third image display areas R1, R2, and R3. A three-dimensional image 13 is displayed in a fourth image display area R4.

Figure 3:
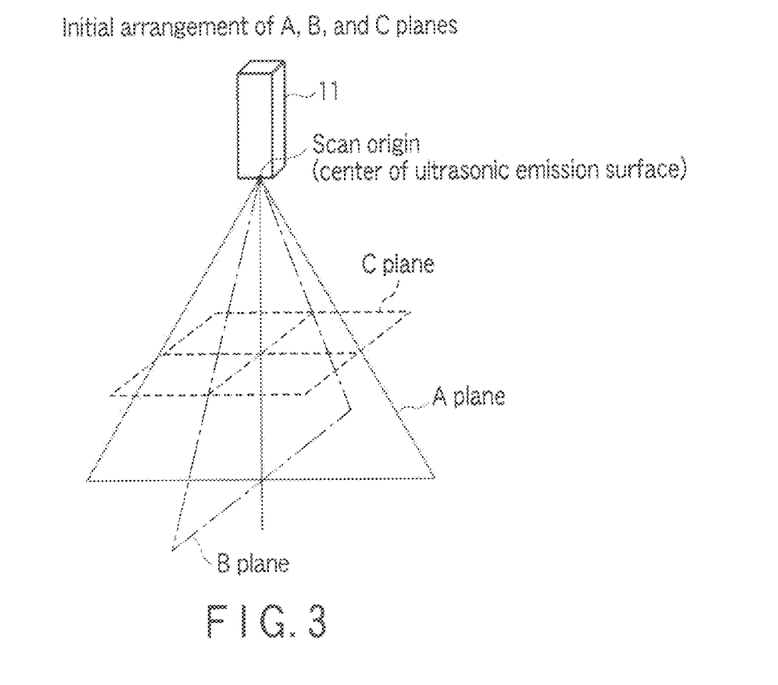
FIG. 3 is a view showing an example of the initial positional relationship between the A, B, and C planes of an MPR image in the initial window displayed on the display unit in FIG. 1.

FIG. 3 is a view showing the initial positional relationship between the A, B, and C planes. As shown in FIG. 3, the A plane represents a slice parallel to an electronic scan plane of the ultrasonic probe. The B plane represents a slice which is perpendicular to the A plane and extends along the array direction of an electronic scan plane. The C plane represents a slice perpendicular to both the A plane and the B plane. Note that the positions of the A, B, and C planes shown in FIG. 3 are the initial positions, and can be arbitrarily changed. Even if, however, the slice positions are changed, the perpendicular relation between the A, B, and C planes is maintained.

When performing ultrasonic scanning, the operator of the ultrasonic probe 11 adjusts the position of the ultrasonic probe 11 to match an electronic scan plane (A plane) with a 4-chamber slice of the heart (a so-called 4-ch view, which is a slice depicting the four chambers of the heart). In this case, the operator adjusts the B plane to a 2-chamber slice (a so-called 2-ch view, which is a slice depicting two of the four chambers of the heart). The operator also adjusts the C plane to a short axis slice of the heart (a slice perpendicular to the left ventricular center axis). However, in the execution of ultrasonic scanning on the heart, the position of the ultrasonic probe 11 is limited to an ultrasonic window at the intercostal position. In many cases, it is not possible to place the ultrasonic probe 11 at the optimal position for an apical approach. For this reason, the initial A and B planes do not often match optimal slices for cardiac observation.

Figure 4:
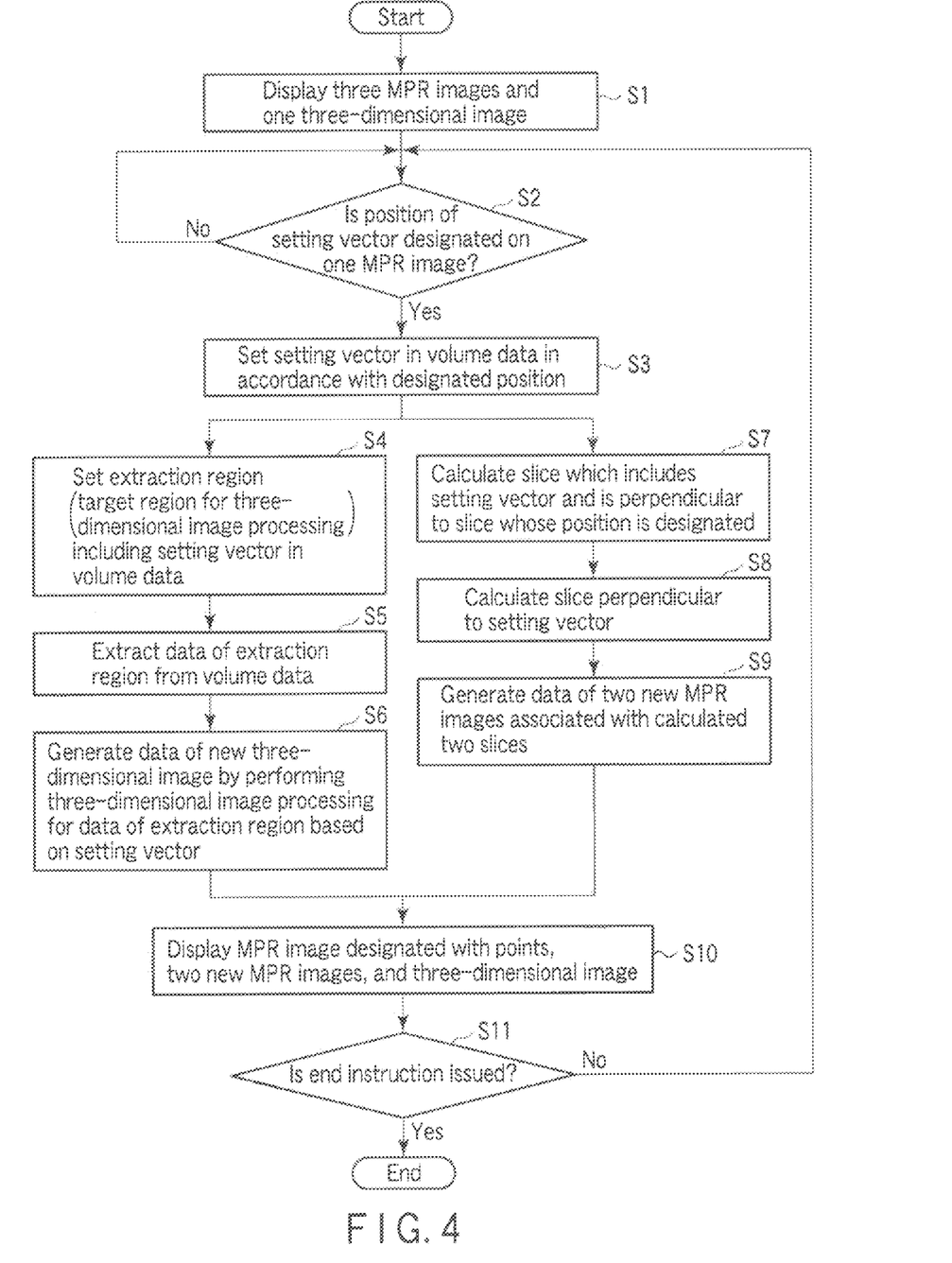
FIG. 4 is a flowchart showing a typical procedure for automatic slice changing processing performed under the control of a system control unit in FIG. 1.

Automatic slice changing processing to be performed under the control of the system control unit 41 will be described next. FIG. 4 is a flowchart showing a typical procedure for automatic slice changing processing.

When the operator issues an instruction to start image observation via the operation unit 39, the system control unit 41 starts automatic slice changing processing. First of all, the system control unit 41 causes the display control unit 35 to perform display processing for an initial window (step S1).

Figure 5:
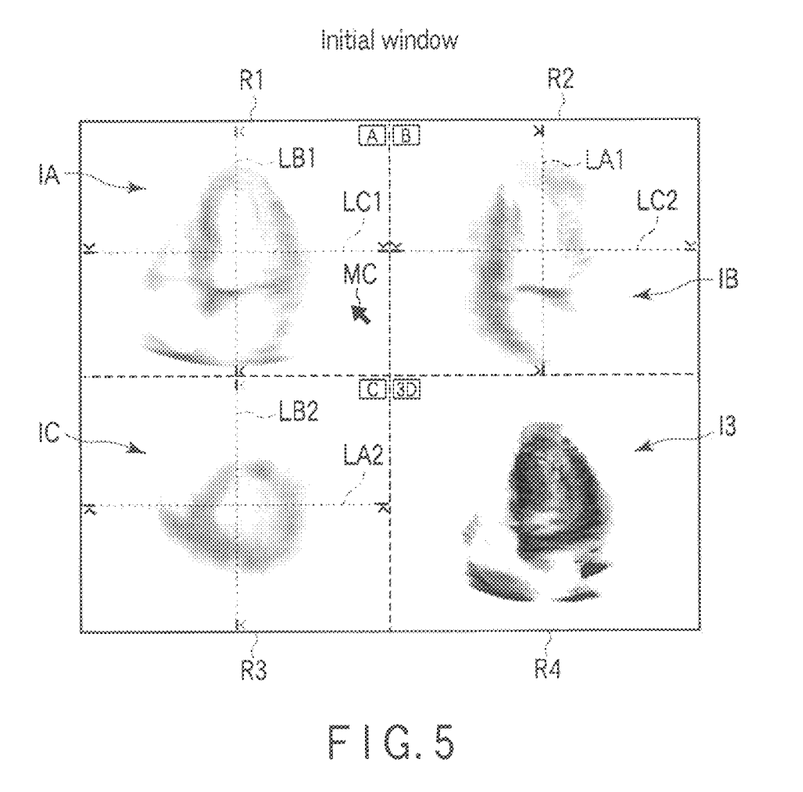
FIG. 5 is a view showing an example of the initial window displayed on the display unit in step S1 in FIG. 4.

In step S1, the display control unit 35 displays the initial window set in a predetermined layout on the display unit 37. FIG. 5 is a view showing an example of the initial window. In the initial window, the initial A plane image IA, the initial B plane image IB, the initial C plane image IC, and the initial three-dimensional image 13 are respectively displayed in the first, second, third, and fourth image display areas R1, R2, R3, and R4. The initial three-dimensional image 13 is a rendered image which is generated from overall volume data and associated with the initial viewing direction. The initial viewing direction can be set to an arbitrary direction, and is set to, for example, a direction which passes through the intersecting line between the A and B planes and is perpendicular to the A plane. The data of the initial A plane image IA, B plane image IB, and C plane image IC are generated by the slice image generation unit 33 in advance. In addition, the initial three-dimensional image data is generated by the three-dimensional image generation unit 29 in advance. Note that no three-dimensional image may be displayed in the fourth display area R4. For example, an MPR image such as an A plane image generated by the slice image generation unit 33 may be displayed or no ultrasonic image may be displayed in this area.

A B plane index line LB1 indicating the position of the B plane on the A plane and a C plane index line LC1 indicating the position of the C plane on the A plane are superimposed on the A plane image IA. An A plane index line LA1 indicating the position of the A plane on the B plane and a C plane index line LC2 indicating the position of the C plane on the B plane are superimposed on the B plane image IB. An A plane index line LA2 indicating the position of the A plane on the C plane and a B plane index line LB2 indicating the position of the B plane on the C plane are superimposed on the C plane image. The display control unit 35 changes the index lines LA1, LA2, LB1, LB2, LC1, and LC2 as slice positions change. In contrast to this, as the operator changes the positions of the index lines LA1, LA2, LB1, LB2, LC1, and LC2 via the operation unit 39, the display control unit 35 changes the corresponding slices.

When the initial window is displayed, the system control unit 41 waits for designation of the position of a setting vector on one of the three MPR images (step S2).

When an initial window is displayed, the operator designates the position of a setting vector via the operation unit 39 to display a three-dimensional image suitable for observation in the fourth image display area. The setting vector is set on one MPR slice of the A, B, and C planes. Typically, the setting vector is set on the A plane to allow the operator of the ultrasonic probe 11 to place the ultrasonic probe 11 such that an electronic scan plane (i.e., the A plane) includes an observation target at the time of ultrasonic scanning.

Figure 6:
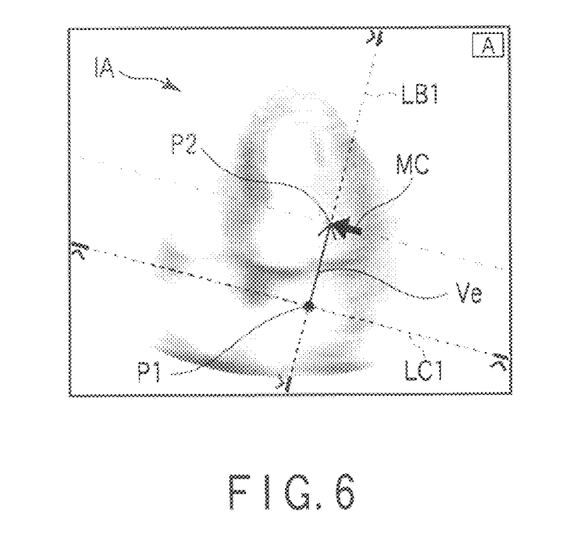
FIG. 6 is a view for explaining setting vector position designation performed in step S2 in FIG. 4.

FIG. 6 is a view for explaining how the position of a setting vector is designated. More specifically, first of all, the operator moves a mouse cursor MC to one point on the A plane image IA via the operation unit 39 and clicks the point. The clicked point is set as a start point P1 of the setting vector. The operator then drags the mouse cursor MC to another point on the A plane image I1 via the operation unit 39. This point is set as an end point P2 of the setting vector. The end point P2 of the setting vector is automatically designated at the position indicated by the mouse cursor MC in real time while the mouse cursor MC is dragged. The vector extending from the start point P1 to the end point P2 is set as a setting vector Ve in step S3.

The manner of how the position of a setting vector is designated will be described by exemplifying a case in which the mitral valve is to be observed. When the mitral valve is to be observed, the center of the mitral valve is observed from the left atrium side or left ventricle side. More specifically, it is preferable to observe the mitral valve from a direction perpendicular to an almost plane of the mitral ring (which means an average plane because the mitral ring has not a planar shape but a saddle-like shape, in general). It is therefore possible to set the start and end points of a setting vector so as to include the range of the motion of the mitral valve on the A plane within a minimum necessary range.

When the operator designates two points (start and end points), the system control unit 41 causes the vector setting unit 25 to perform setting processing for a setting vector (step S3). In step S3, the vector setting unit 25 sets the vector extending from the designated start point to the designated end point as a setting vector. The set setting vector is three-dimensionally set on volume data. Since the start and end points of the setting vector are designated on the A plane image, the setting vector is included in the A plane in the volume data. As shown in FIG. 6, the display control unit 35 displays the setting vector Ve on the A plane image in real time.

Figure 7:
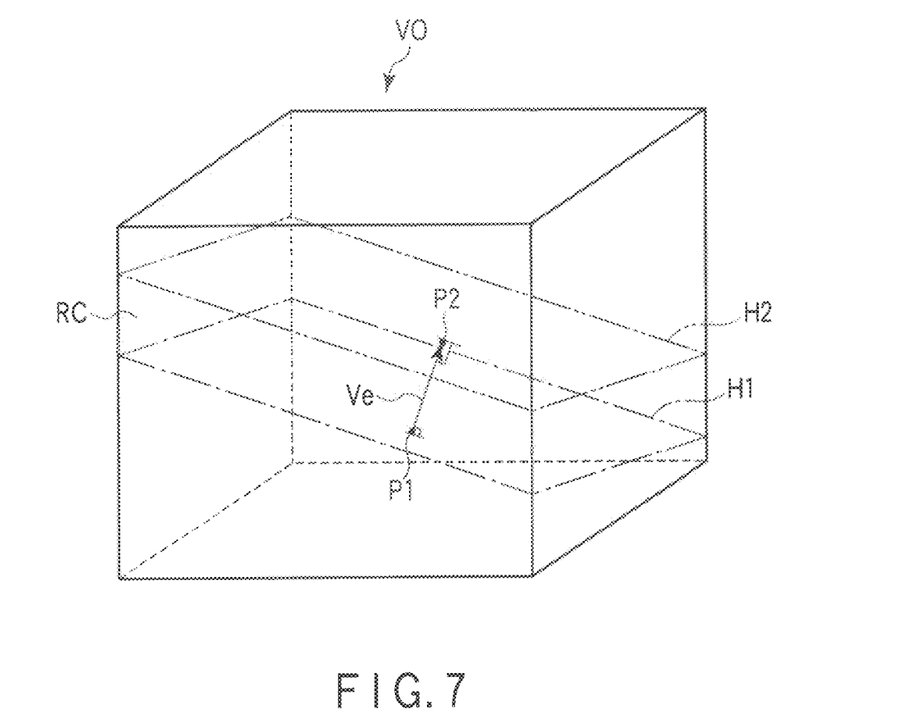
FIG. 7 is a view for explaining extraction region setting processing performed in step S4 in FIG. 4.

Upon completion of step S3, the system control unit 41 causes the extraction unit 27 to perform setting processing for an extraction region (step S4). In step S4, the extraction unit 27 sets the range indicated by the setting vector as an extraction region. FIG. 7 is a view for explaining extraction region setting processing. As shown in FIG. 7, the extraction unit 27 sets, as an extraction region RC, a region in volume data VO which is sandwiched between a first plane H1 including the start point and a second plane H2 including the end point. The first plane H1 includes a start point P1 and is set at a position perpendicular to the setting vector Ve. The second plane H2 includes an end point P2 and is set at a position perpendicular to the setting vector Ve.

Upon completion of step S4, the system control unit 41 causes the extraction unit 27 to perform extraction processing for an extraction region (step S5). In step S8, the extraction unit 27 extracts (crops) the data of an extraction region from the volume data.

Upon completion of step S5, the system control unit 41 causes the three-dimensional image generation unit 29 to perform three-dimensional image processing (step S6). In step S6, the three-dimensional image generation unit 29 performs three-dimensional image processing for the data of the extraction region to generate the data of a three-dimensional image having the setting vector in the viewing direction. As three-dimensional image processing, volume rendering, surface rendering, MIP (Minimum Intensity Projection), or the like is used. The operator can arbitrarily set the type of three-dimensional image to be used via the operation unit 39.

Upon completion of step S3, the system control unit 41 also causes the slice calculation unit 31 to perform first slice calculation processing (step S7).

Figure 8:
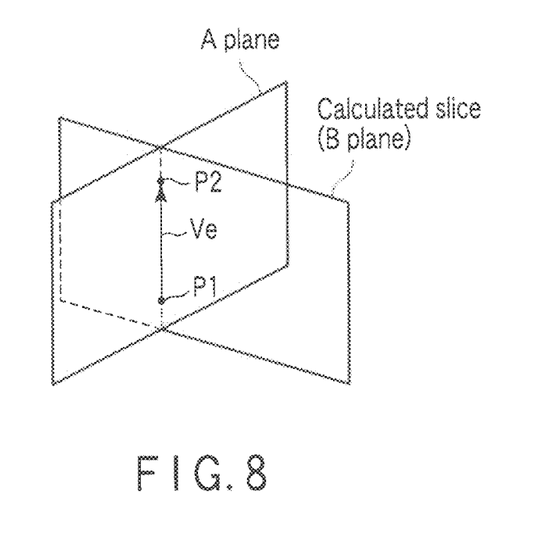
FIG. 8 is a view for explaining first slice calculation processing performed in step S7 in FIG. 4.

FIG. 8 is a view for explaining the first slice calculation processing. As shown in FIG. 8, in step S7, the slice calculation unit 31 calculates a slice (calculated slice) which includes the setting vector Ve and is perpendicular to an MPR slice (the A plane in this embodiment) designated with points. That is, the slice calculation unit 31 calculates the position of the calculated slice which includes both the start and end points P1 and P2 of the setting vector Ve and is perpendicular to the MPR slice designated with points. The calculated slice having the calculated position is set as a new B plane.

Upon completion of step S7, the system control unit 41 causes the slice calculation unit 31 to perform second slice calculation processing (step S8).

Figure 9:
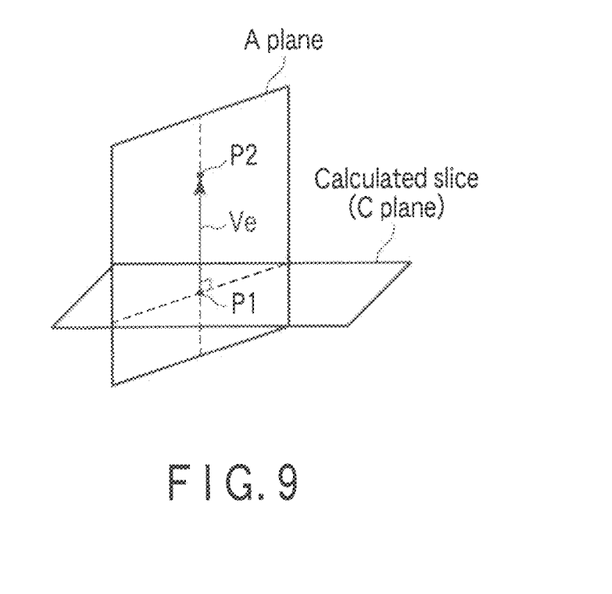
FIG. 9 is a view for explaining second slice calculation processing performed in step S8 in FIG. 4.

FIG. 9 is a view for explaining the second slice calculation processing. As shown in FIG. 9, in step S8, the slice calculation unit 31 calculates the position of a slice (calculated slice) which intersects the start point P1 of the setting vector Ve and has the setting vector Ve as a normal vector. That is, the slice calculation unit 31 calculates the position of a calculated slice which is perpendicular to the setting vector Ve at the start point P1 of the setting vector Ve. The calculated slice in step S8 is perpendicular to both the slice designated with points (the A plane in this case) and the calculated slice in step S7 (the B plane in this case). The calculated slice having the calculated position is set as a new C plane. That is, the new C plane is set to coincide with an end face of the extraction region.

In this manner, in steps S7 and S8, the slice calculation unit 31 calculates the position of a slice which intersects the setting vector and is perpendicular to the slice (the A plane in this case) with the position of the setting vector being designated with points.

Upon completion of step S8, the system control unit 41 causes the slice image generation unit 33 to perform MPR processing (step S9). In step S9, the slice image generation unit 33 performs MPR processing for the volume data to generate the data of a B plane image associated with the B plane having the position calculated in step S7. The slice image generation unit 33 also performs MPR processing for the volume data to generate the data of a C plane image associated with the C plane having the position calculated in step S8.

Upon completion of steps S6 and S9, the system control unit 41 causes the display control unit 35 to perform display processing (step S10). In step S10, the display control unit 35 displays the MPR image (the A plane image in this case) designated with points in step S2, the two MPR images (the B and C plane images in this case) generated in step S6, and the three-dimensional image generated in step S9.

Figure 10:
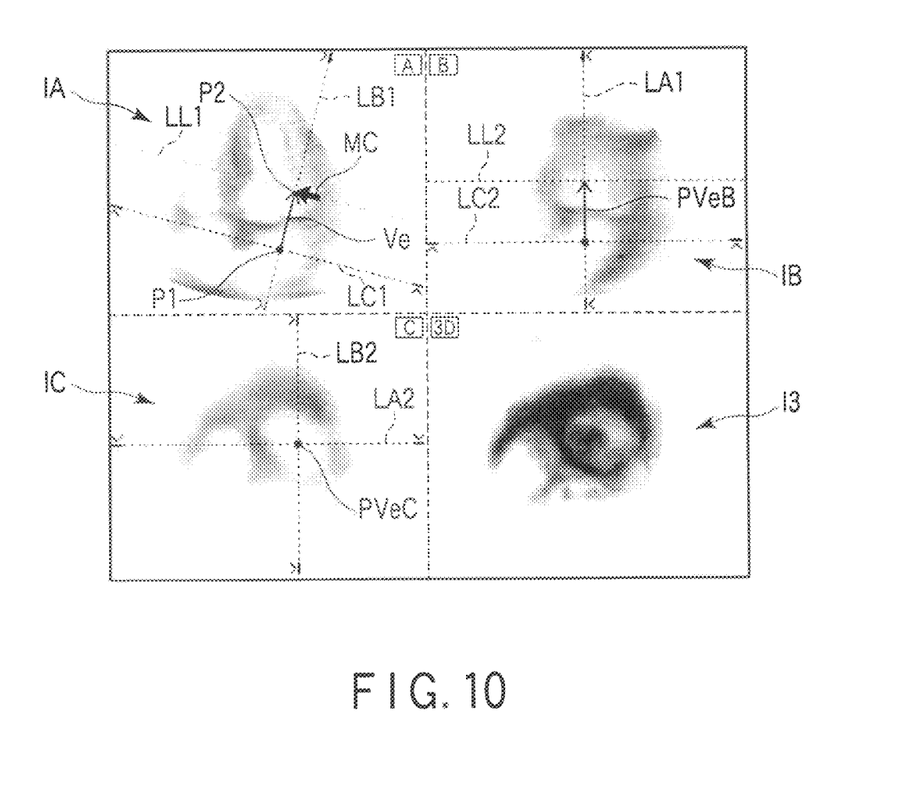
FIG. 10 is a view showing an example of the window displayed on the display unit in step S10 in FIG. 4.

FIG. 10 is a view showing an example of the window displayed in step S10. As shown in FIG. 10, the A plane image IA like the initial window is displayed in the first image display area R1. The B plane image IB associated with the B plane calculated in step S7 is displayed in the second image display area R2. The C plane image IC associated with the C plane calculated in step S8 is displayed in the third image display area R3. That is, the display control unit 35 changes the positions of slices of MPR images on which no setting vector is set via the operation unit 39 (in this case, the MPR image on which the setting vector is set via the operation unit 39 is the A plane image, and the MPR images on which no setting vector is set are the B and C plane images) to the positions which intersect the setting vector and are perpendicular to the slice of the MPR image on which the setting vector is set via the operation unit 39. The display control unit 35 also updates the displayed three-dimensional image in accordance with the settings of the setting vector.

The display control unit 35 also changes the B plane index line LB1 on the A plane image IA and the B plane index line LB2 on the C plane image IC in accordance with the position of the B plane calculated in step S7. Likewise, the display control unit 35 changes the C plane index line LC1 on the A plane image IA and the C plane index line LC2 on the B plane image IB in accordance with the position of the C plane calculated in step S8. The display control unit 35 also changes the A plane index line LA1 on the B plane image IB and the A plane index line LA2 on the C plane image IC in accordance with the positions of the B and C planes.

In addition, the display control unit 35 draws, on the B plane image IB, a projection PVeB (to be referred to as a projection vector hereinafter) on the B plane of the setting vector Ve to indicate the position and length of the setting vector Ve on the B plane. Likewise, the display control unit 35 draws, on the C plane image IC, a projection vector PVeC of the setting vector Ve on the C plane to indicate the position and length of the setting vector Ve on the C plane. It is possible to arbitrarily change the positions and lengths of the projection vectors PVeB and PVeC via the operation unit 39. The vector setting unit 25 re-sets the position and length of the setting vector in accordance with changes in the positions and lengths of the projection vectors PVeB and PVeC.

The display control unit 35 also displays boundary lines indicating the boundary of the extraction region on each of the MPR images IA and IB. More specifically, the display control unit 35 displays, on the A plane image IA, a boundary line (identical to the B plane index line LC1) indicating the position of the first plane (including the start point P1) of the extraction region and a boundary line LL1 indicating the position of the second plane (including the end point P2) of the extraction region. The display control unit 35 displays, on the B plane image IB, a boundary line (identical to the B plane index line LC2) indicating the position of the first plane of the extraction region and a boundary line LL2 indicating the position of the second plane of the extraction region. It is possible to arbitrarily change the position of each boundary line via the operation unit 39. The range of the extraction region is re-set in accordance with a change in the position of each boundary line.

The new C plane image like that described above is an MPR image associated with an end face of the extraction region. Observing this new C plane image therefore allows the operator to easily comprehend the form of the three-dimensional image.

Upon completion of step S10, the system control unit 41 waits for issuance of an end instruction by the operator via the operation unit 39 (step S11). If no end instruction issued, the system control unit 41 advances to step S2 again to wait for designation of the position of a setting vector (second execution of step S2). When the operator re-designates the position of a setting vector via the operation unit 39, the system control unit 41 performs steps S4 to S11 again. In this manner, the operator adjusts the position of a setting vector while changing the slice to be designated with points, until an optimal setting vector is three-dimensionally set.

Re-setting of this setting vector will be described in detail below. Assume that when the position of a setting vector is designated on the A plane in first step S2, the position of the setting vector on the A plane in the volume data is set at an optimal position. However, it is not possible to designate the position of the setting vector on the B and C planes by only designating the position of the setting vector on the A plane. In the second execution of step S2, therefore, it is necessary to designate the position of the setting vector on the B and C planes.

Figure 11:
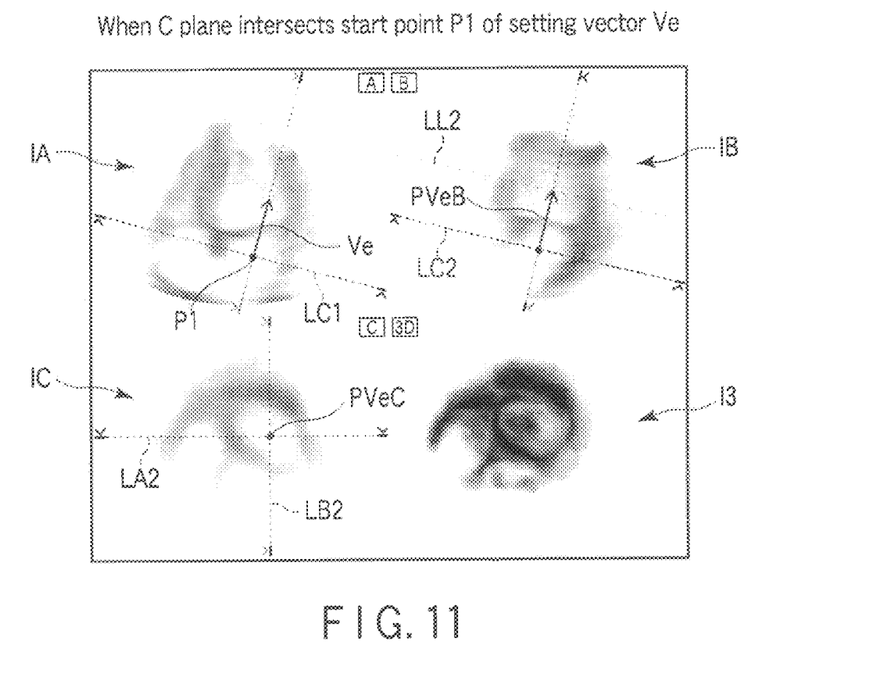
FIG. 11 is a view for explaining setting vector adjustment processing in the second execution of step S2 in FIG. 4 (when a C plane intersects the start point of a setting vector)

As shown in FIG. 11, for example, the operator corrects the position of the setting vector on the B plane by adjusting the position of the projection PVeB drawn on the B plane image IB. The three-dimensional position of the setting vector is changed in accordance with a change in the projection vector PVeB. Note that the display control unit 35 draws, on the A plane image IA, the projection of the changed setting vector on the A plane, and draws, on the C plane image IC, the projection of the setting vector on the C plane. Note that the position of the setting vector on the C plane is corrected on the C plane image IC by translating the C plane along the crossing line between the A and B planes via the operation unit 39.

At the beginning of the second execution of step S2, the B plane is automatically set at a position where it includes the setting vector, and the C plane is automatically set at a position where it is perpendicular to the start point of the setting vector. In the second execution of step S2, therefore, setting the position of the setting vector on the B and C planes will set the setting vector at a desired three-dimensional position in effect. That is, according to this embodiment, designating the position of a setting vector at least twice can set the setting vector at a desired three-dimensional position. In addition, when correcting the setting vector on the B and C planes, it is possible to correct the setting vector on the B plane without greatly changing the position of the setting vector set on the A plane.

Steps S2 to S11 are repeated until a setting vector is set at an optimal three-dimensional position in this manner. When the operator issues an end instruction via the operation unit 39 or the like (YES in step S11), the system control unit 41 terminates the automatic slice changing processing.

Figure 12:
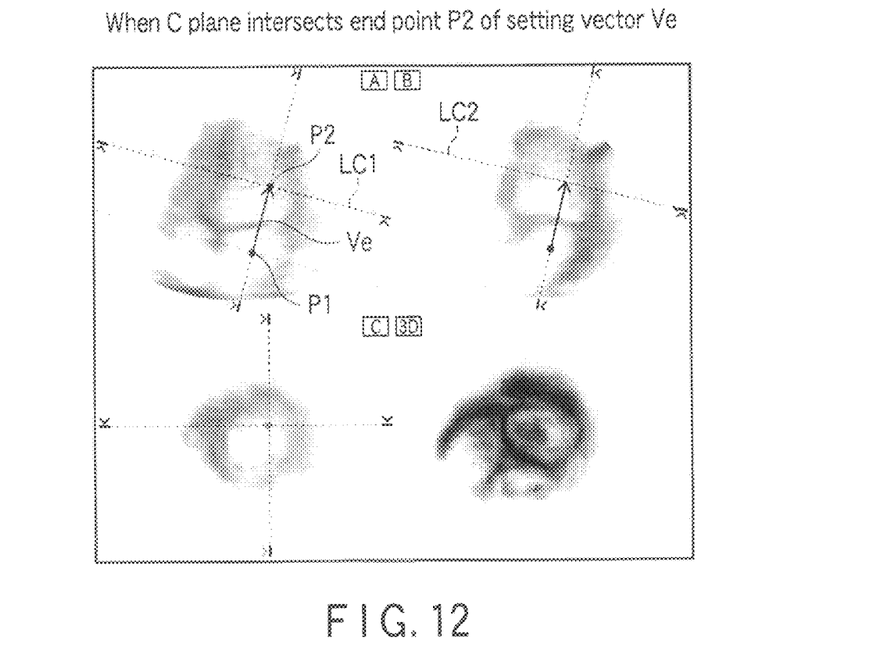
FIG. 12 is a view showing an example of a C plane image associated with a C plane intersecting the end point of the setting vector displayed on the display unit in FIG. 1.
Figure 13:
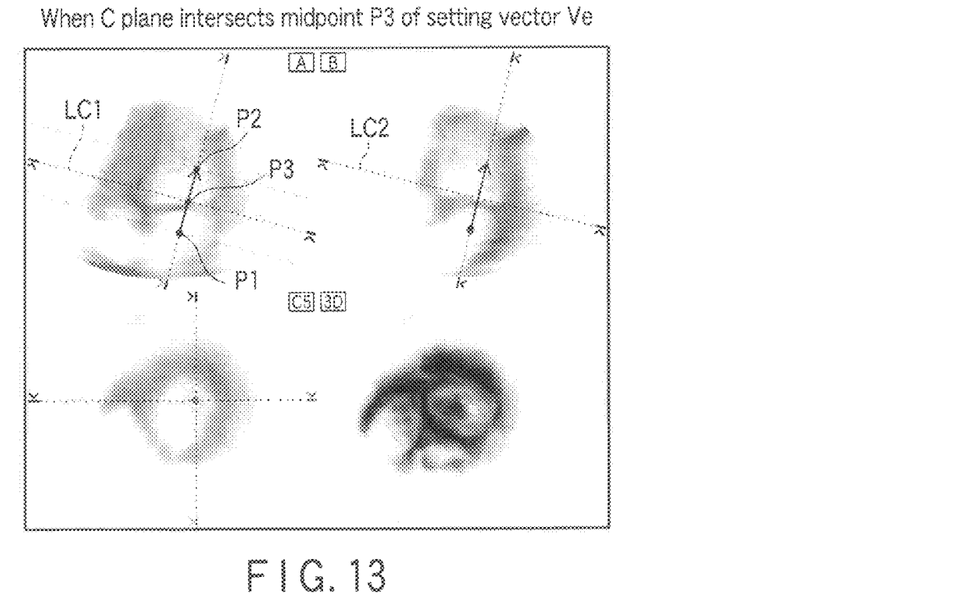
FIG. 13 is a view showing an example of a C plane image associated with a C plane intersecting the midpoint of the setting vector displayed on the display unit in FIG. 1.
Figure 14:
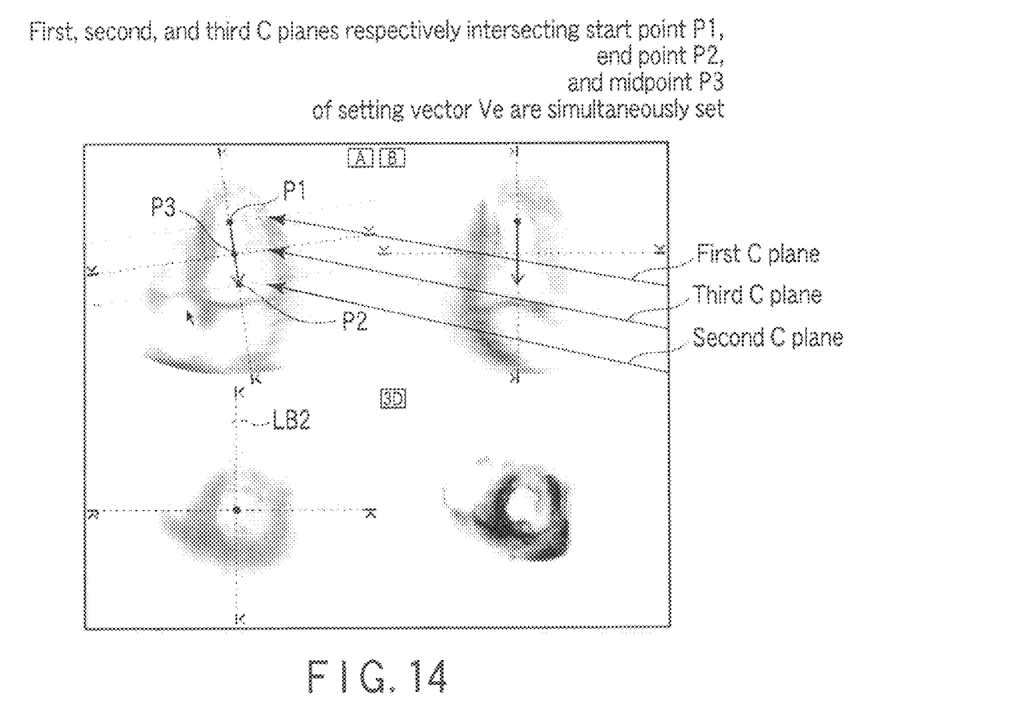
FIG. 14 is a view showing an example of the window displayed by the display unit in FIG. 1 when a C plane intersecting the start point of a setting vector, a C plane intersecting the end point of the vector, and a C plane intersecting the midpoint of the vector are set altogether.

According to the above description, the C plane is set at a position where it intersects the start point of a setting vector and is perpendicular to the setting vector. However, this embodiment is not limited to this. As shown in FIG. 12, for example, the C plane may be set at a position where it intersects the end point P2 of the setting vector Ve and is perpendicular to the setting vector Ve. As shown in FIG. 13, the C plane may be set at a position where it intersects a midpoint P3 of the setting vector Ve and is perpendicular the setting vector Ve. In addition, when using a plurality of C planes associated with a plurality of positions, for example, three C planes, it is possible to set the first C plane intersecting the start point P1 of the setting vector Ve, the second C plane intersecting the midpoint P3, and the third C plane intersecting the end point P2, as shown in FIG. 14. The three C planes are effective in observing short-axis images near the apex, center, and valve ring of the left ventricle. This embodiment implements simplification of setting operation for such three C planes. This is because it is possible to automatically set three C planes as well as an A plane (4-ch view) and a B plane (2-ch view) by only making the operator designate two points with the mouse cursor in step S2.

With the above arrangement, when setting a setting vector, the ultrasonic diagnostic apparatus 1 and ultrasonic image processing apparatus 50 according to this embodiment automatically change MPR slices other than the MPR slice on which the position of the setting vector is designated with points so as to make them perpendicular to the setting vector. This allows the operator to adjust the position of a setting vector on the remaining MPR images without changing the slice positions of the remaining MPR images. In this manner, the ultrasonic diagnostic apparatus 1 and the ultrasonic image processing apparatus 50 implement the simplification of adjustment of setting vectors.

In this manner, the ultrasonic diagnostic apparatus 1, the ultrasonic image processing apparatus 50, and the ultrasonic image processing method improve operability in image observation using ultrasonic images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic image processing apparatus, comprising:
a memory configured to store volume data generated by ultrasonic scanning;
a processing circuit configured to
generate, from the volume data, data of a plurality of slice images corresponding to a plurality of slices; and
generate, from the volume data using a predetermined viewing direction, data of a three-dimensional image; and
a display configured to display the slice images and the three-dimensional image, wherein the processing circuit is further configured to
set a vector on a first slice image of the displayed slice images in accordance with an instruction from an operator, the first slice image corresponding to a first slice of the plurality of slices;
change a position defining a second slice of the plurality of slices and a position defining a third slide of the plurality of slices, the second slice corresponding to a second slice image of the displayed slice images, the third slice corresponding to a third slice image of the displayed slice images, so that the second slice includes the set vector indicating an extraction region and a viewing direction and is perpendicular to the first slice, and the third slice intersects the set vector at a predetermined point; and
update the displayed three-dimensional image based on the set vector indicating the extraction region and the viewing direction, and update the second and third images based on the changed second and third slices.

2. The apparatus according to claim 1, wherein the processing circuit is further configured to change the position of the second slice to a plane that includes the set vector.

3. The apparatus according to claim 1, wherein the processing circuit is configured to change the position of the third slice to a plane that intersects the predetermined point, wherein the predetermined point is one of a start point, a midpoint, and an end point of the set vector.

4. The ultrasonic image processing apparatus of claim 1, wherein the processing circuit is configured to generate three multiplanar reconstruction (MPR) slice images as the plurality of slice images.

5. The ultrasonic image processing apparatus of claim 4, wherein the processing circuit is further configured to cause the display to display the three MPR images prior to setting the vector, and wherein the processing circuit is further configured to modify, when the set vector is set on one of the MPR images, positions of the other two MPR images.

6. An ultrasonic image processing apparatus, comprising:
a memory configured to store volume data generated by ultrasonic scanning;
a processing circuit configured to
generate, from the volume data, data of a first slice image corresponding to a first slice;
set a vector on the first slice image in accordance with an instruction from an operator;
extract data of a region including the vector from the volume data;
generate, from the extracted region, data of a three-dimensional image, with the vector defining a viewing direction;
calculate, in the volume data, a second slice and a third slice, so that the second slice includes the set vector and is perpendicular to the first slice, and the third slice intersects the set vector at a predetermined point;
generate, from the volume data, data of a second slice image associated with the second slice; and
generate, from the volume data, data of a third slice image associated with the third slice; and
a display configured to display the second slice image, the third slice image, and the three-dimensional image.

7. An ultrasonic diagnostic apparatus, comprising:
an ultrasonic probe;
a scanning circuit configured to scan a subject with ultrasonic waves via the ultrasonic probe;
a processing circuit configured to
generate volume data associated with the subject from an echo signal from the ultrasonic probe;
generate, from the volume data, data of a plurality of slice images corresponding to a plurality of slices; and
generate, from the volume data using a predetermined viewing direction, data of a three-dimensional image; and
a display configured to display the slice images and the three-dimensional image, wherein the processing circuit is further configured to
set a vector on a first slice image of the displayed slice images in accordance with an instruction from the operator, the first slice image corresponding to a first slice of the plurality of slices;
change a position defining a second slice of the plurality of slices and a position defining a third slice of the plurality of slices, the second slice corresponding to a second slice image of the displayed slice images, the third slice corresponding to a third slice image of the displayed slice images, so that the second slice includes the set vector indicating an extraction region and a viewing direction and is perpendicular to the first slice, and the third slice intersects the set vector at a predetermined point; and
update the displayed three-dimensional image based on the set vector indicating the extraction region and the viewing direction, and update the second and third images based on the changed second and third slices.

8. An ultrasonic diagnostic apparatus, comprising:
an ultrasonic probe;
a scanning circuit configured to scan a subject with ultrasonic waves via the ultrasonic probe;
a processing circuit configured to
generate volume data associated with the subject from an echo signal from the ultrasonic probe;

generate, from the volume data, data of a first slice image corresponding to a first slice;
set a vector on the first slice image in accordance with an instruction from an operator;
extract a region including the vector from the volume data;
generate, using the extracted region, data of a three-dimensional image with the vector defining a viewing direction;
calculate, in the volume data, a position of a second slice and a third slice, so that the second slice includes the set vector and is perpendicular to the first slice, and the third slice intersects the set vector at a predetermined point;
generate, from the volume data, data of a second slice image corresponding to the second slice; and
generate, from the volume data, data of a third slice image associated with the third slice; and
a display configured to display the second slice image and the three-dimensional image.

* * * * *